United States Patent
Sun et al.

(10) Patent No.: US 9,603,790 B2
(45) Date of Patent: Mar. 28, 2017

(54) COSMETIC COMPOSITIONS COMPRISING MARINE PLANTS

(71) Applicant: BASF Corporation, Florham Park, NJ (US)

(72) Inventors: Yuhua Sun, Stony Brook, NY (US); Manasi Chavan, Stony Brook, NY (US)

(73) Assignee: BASF CORPORATION, Florham Park, NJ (US)

( * ) Notice: Subject to any disclaimer, the term of this patent is extended or adjusted under 35 U.S.C. 154(b) by 385 days.

(21) Appl. No.: 14/077,934

(22) Filed: Nov. 12, 2013

(65) Prior Publication Data

US 2014/0141035 A1    May 22, 2014

Related U.S. Application Data

(60) Provisional application No. 61/726,722, filed on Nov. 15, 2012.

(51) Int. Cl.
| | | |
|---|---|---|
| *A61K 36/03* | (2006.01) | |
| *A61K 8/97* | (2017.01) | |
| *A61Q 19/00* | (2006.01) | |
| *A61Q 19/08* | (2006.01) | |

(52) U.S. Cl.
CPC .............. *A61K 8/975* (2013.01); *A61Q 19/00* (2013.01); *A61Q 19/08* (2013.01); *A61K 2800/78* (2013.01)

(58) Field of Classification Search
None
See application file for complete search history.

(56) References Cited

U.S. PATENT DOCUMENTS

| | | |
|---|---|---|
| 5,508,033 A | 4/1996 | Briand |
| 7,128,914 B2 | 10/2006 | Leclerc et al. |
| 7,220,517 B2 | 5/2007 | Park et al. |
| 2004/0223942 A1 | 11/2004 | Fujimura |
| 2007/0248563 A1 | 10/2007 | Iovanni |
| 2009/0142370 A1 | 6/2009 | Shih et al. |
| 2010/0047219 A1 | 2/2010 | Ceccoli et al. |
| 2010/0316720 A1 | 12/2010 | Stutz et al. |
| 2012/0195923 A1 | 8/2012 | Turgeon et al. |
| 2013/0017537 A1 | 1/2013 | Bonnet |

FOREIGN PATENT DOCUMENTS

| | | | |
|---|---|---|---|
| JP | 2001031557 A | * | 2/2001 |
| KR | 2010-0102389 A1 | | 9/2010 |
| WO | 2011/097572 A1 | | 8/2011 |

OTHER PUBLICATIONS

Fujimura et al., Journal of Cosmetic Science, Jan.-Feb. 2002, vol. 53. No. 1, pp. 1-9.
English language abstract of KR 2010-0102389.
International Search Report dated Feb. 24, 2014.
Nn: "Fucus Vesiculosus Extract / Fucus Vesiculsus Powder" In: "International Cosmetic Ingredient Dictionary and Handbook, 13th edition" Jan. 1, 2010 (Jan. 1, 2010), Personal Care Products Council, Washington D.C., USA XP055257068, pp. 1134-1135.
Database GNPD [online] MINTEL; Oct. 1, 2010 (Oct. 1, 2010), Mixima Inc.: "Vis Clair Firming Eye Complex", XP002755402, Database accession No. 1427979.
Choi, Chun Yeon, et al. "Alaria esculenta extract protects against oxidative damage by inducing heme oxygenase-1 expression via Akt and Nrf2." Molecular & Cellular Toxicology 5 (2009): 120-125.

* cited by examiner

*Primary Examiner* — Chris R Tate
*Assistant Examiner* — Randall Winston
(74) *Attorney, Agent, or Firm* — Lowenstein Sandler LLP

(57) ABSTRACT

The present invention relates to a cosmetic active ingredient for improving the appearance of the skin beneath the eyes. More particularly, the present invention relates to a cosmetic active ingredient comprising an extract of the marine algae, *Fucus vesiculosus*. The present invention also relates to topical cosmetic compositions comprising as an active component an extract of the marine algae, *Fucus vesiculosus*, alone or in combination with additional cosmetic active ingredients, to reduce the appearance of dark circles in skin beneath the eye.

10 Claims, 7 Drawing Sheets

FIG. 1-A
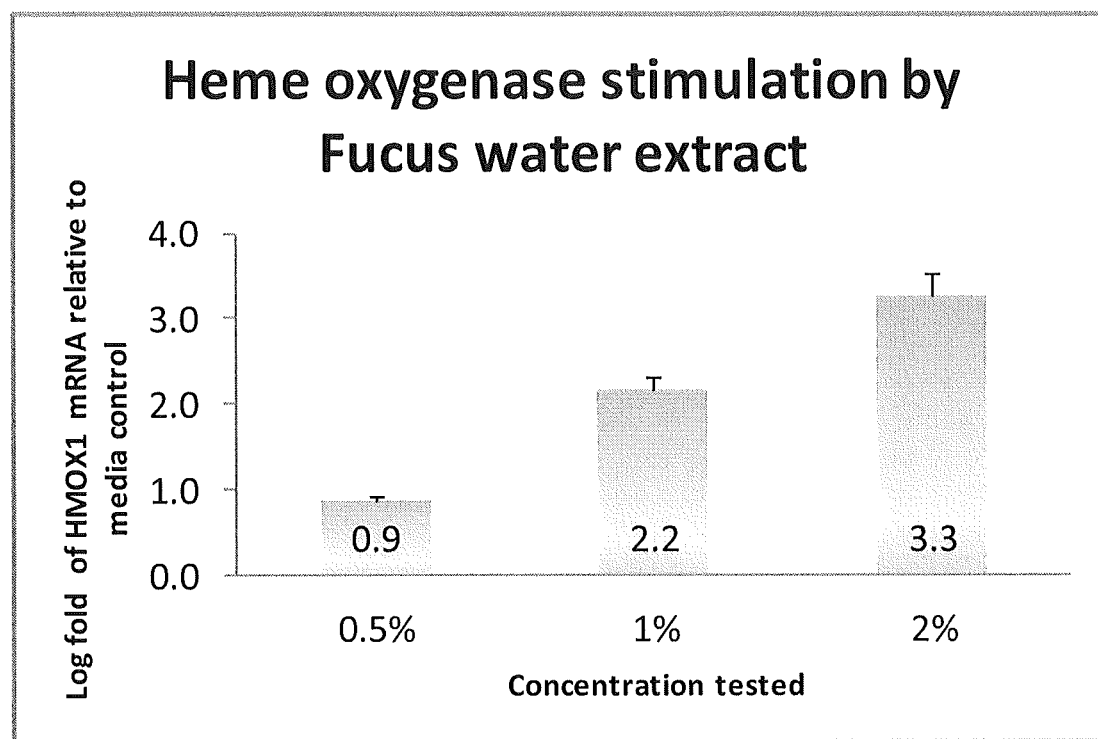

FIG. 1-B
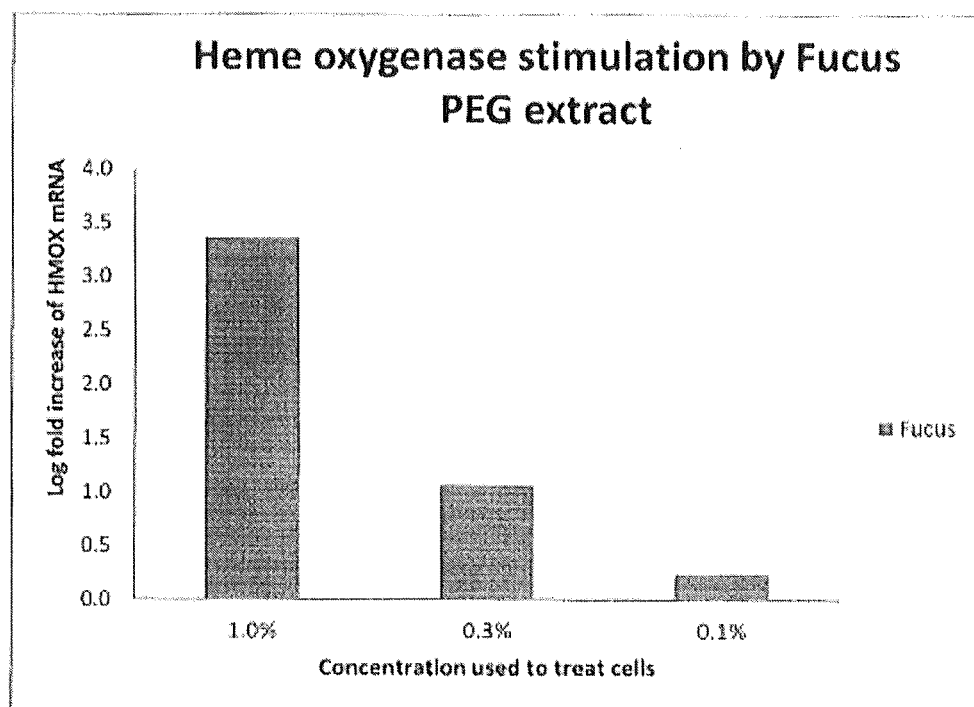

FIG. 2-A
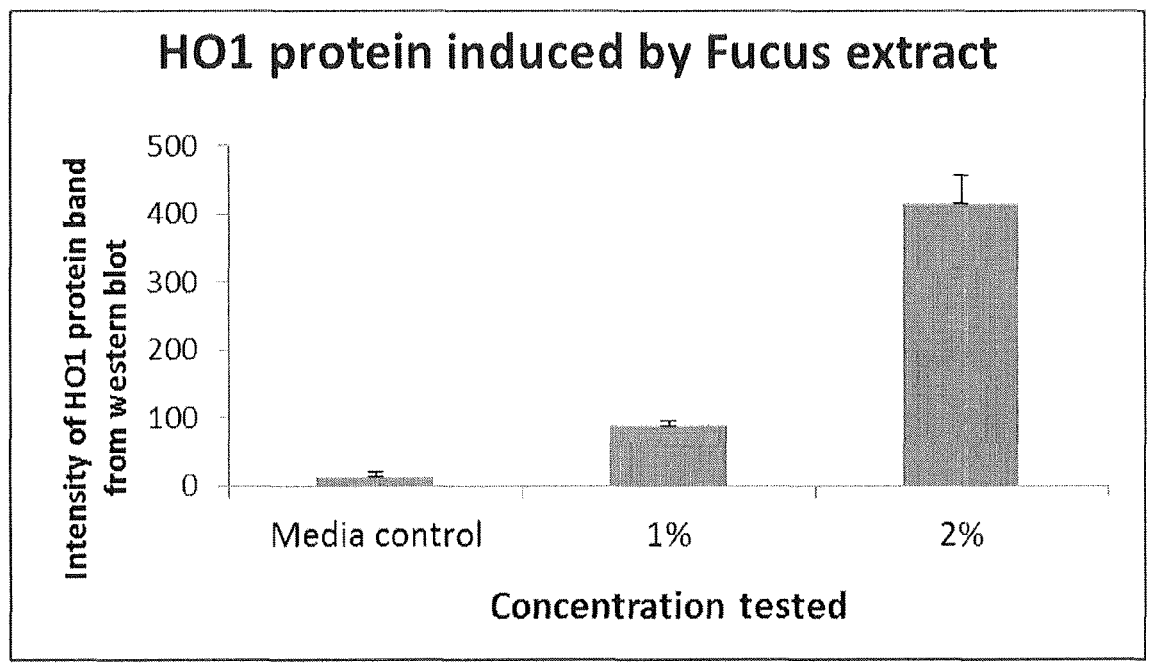

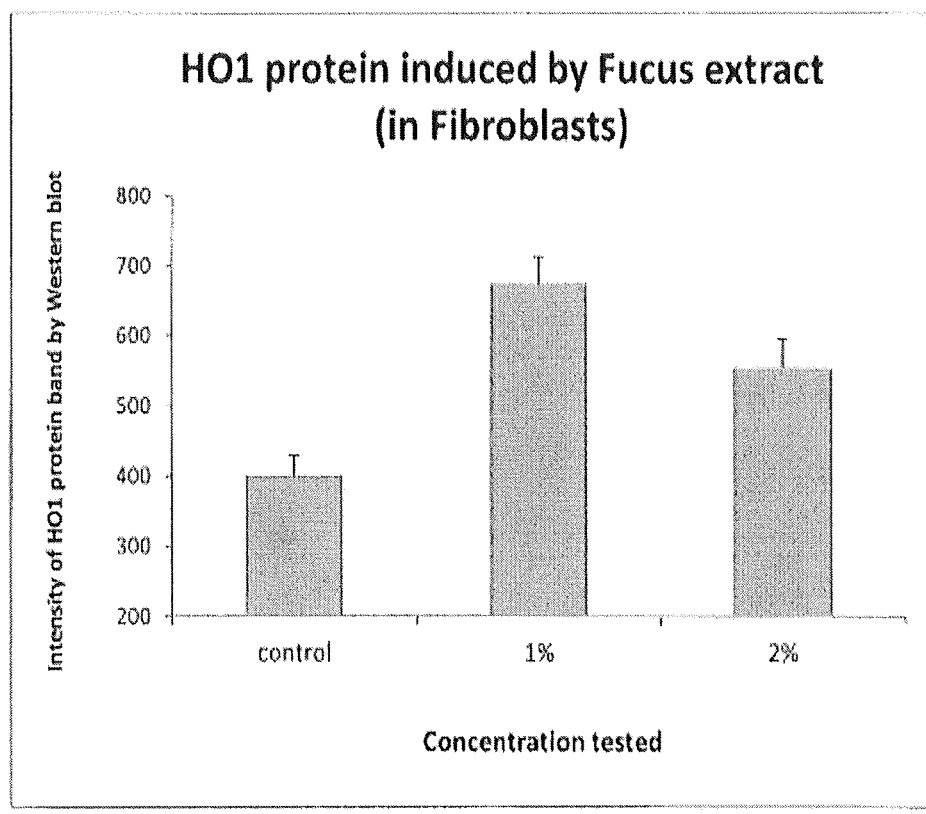
FIG. 2-B

COSMETIC COMPOSITIONS COMPRISING MARINE PLANTS

CROSS REFERENCE TO RELATED APPLICATION

The present application claims the benefit of provisional application Ser. No. 61/726,722, filed Nov. 15, 2012, for all useful purposes, and the specification and drawings thereof are incorporated herein by reference.

FIELD OF THE INVENTION

The present invention relates to a cosmetic active ingredient for improving the appearance of the skin beneath the eyes, including the appearance of dark circles in skin beneath the eye by increasing the activity of heme oxygenase type 1 in such skin. More particularly, the present invention relates to a cosmetic active ingredient comprising an extract of the marine algae, *Fucus vesiculosus*.

The present invention also relates to topical cosmetic compositions comprising as an active component an extract of the marine algae, *Fucus vesiculosus*, alone or in combination with additional cosmetic active ingredients, to reduce the appearance of dark circles in skin beneath the eye.

BACKGROUND OF THE INVENTION

Dark circles in skin beneath the eye can contribute to an overall appearance of fatigue and/or aging and it is highly desirable to reduce the appearance of such circles in order to effect a more youthful and energetic look. Thus, a multitude of cosmetic or skin care products exist in the marketplace with claims to reduce the appearance of these dark circles.

Such dark circles are attributed to a number of causes, but are mainly the result of heme catabolite, inflammation, and melanin accumulation. Heme is the prosthetic group of heme proteins, such as hemoglobin, a major component of blood. Heme is leaked by dilated blood vessels and becomes free heme, which catalyze the production of free radicals and is pro-inflammatory and pro-oxidative. Heme oxygenase is a rate limiting enzyme that catalyzes the degradation of heme to biliverdin which is subsequently converted to bilirubin, carbon monoxide and iron which will be stored in ferritin, all of which have well described antioxidant and anti-inflammatory properties. Heme oxygenase 1 (HO-1) is an inducible isoform. Stimulating HO-1 would, in turn, stimulate the scavenging of heme thereby reducing the appearance of dark circles. It is therefore desirable to have a cosmetic active ingredient which is capable of stimulating the production of HO-1 in the skin under the eyes.

Further, many cosmetic compositions which address dark circles address additional skin imperfections occurring in the eye area in order to further reduce the "tired eyes" appearance. For example, products addressing dark circles often further address puffiness (i.e, "eye bags"), wrinkles, and dryness in the eye area. To do so, the product generally contains multiple cosmetic active ingredients, each directed to one of the specific type of imperfections. The use of multiple active ingredients increases the difficulty in formulating such products as well as increases the raw material costs. Thus, it is desirable to have a single cosmetic active ingredient which is capable of addressing multiple cosmetic concerns associated with the eye area.

SUMMARY OF THE INVENTION

*Fucus vesiculous*, also commonly known as bladderwrack or rock weed, is a species of temperate algae naturally found in littoral/lower intertidal zones along the coastlines of the Atlantic Oceans. It can also found in some Pacific ocean regions as well as the North Sea and Baltic Sea.

It was unexpectedly discovered that an extract of the marine plant, *Fucus vesiculosus*, stimulates the expression of HO-1 in skin thereby assisting in the removal of heme catabolites known to be responsible for dark circles under the eye. It was also unexpectedly discovered that such extract also has as an added benefit anti-inflammatory properties which can reduce the vasodialation of blood vessels and reduce the leakage of heme, and anti-oxidative properties which further improve the appearance of eye bags and wrinkles. Such extract also stimulates collagen production thereby reducing the appearance of fine lines and wrinkles in skin under and around the eye area.

Thus, through the topical application of compositions comprising *Fucus* extract, it is possible to address multiple cosmetic concerns relating to the eye area and provide a more youthful and energized appearance to the eyes.

Other aspects and objectives of the present invention will become more apparent from the following description, examples and claims.

FIGURES

FIG. 1-A is a graph showing the stimulation of HO1 gene expression by an aqueous *Fucus vesiculosis* extract at varying concentrations.

FIG. 1-B is a graph showing the stimulation of HO1 gene expression by a *Fucus vesiculosis* PEG extract at varying concentrations.

FIG. 2-A is a graph showing the stimulation of HO1 protein expression in keratinocytes by *Fucus vesiculosis* extract.

FIG. 2-B is a graph showing the stimulation of HO1 protein expression in fibroblasts by *Fucus vesiculosis* extract FIG. 3 is a further graph showing the anti-oxidation efficacy of *Fucus vesiculosis* extract.

DETAILED DESCRIPTION

Figure 3:
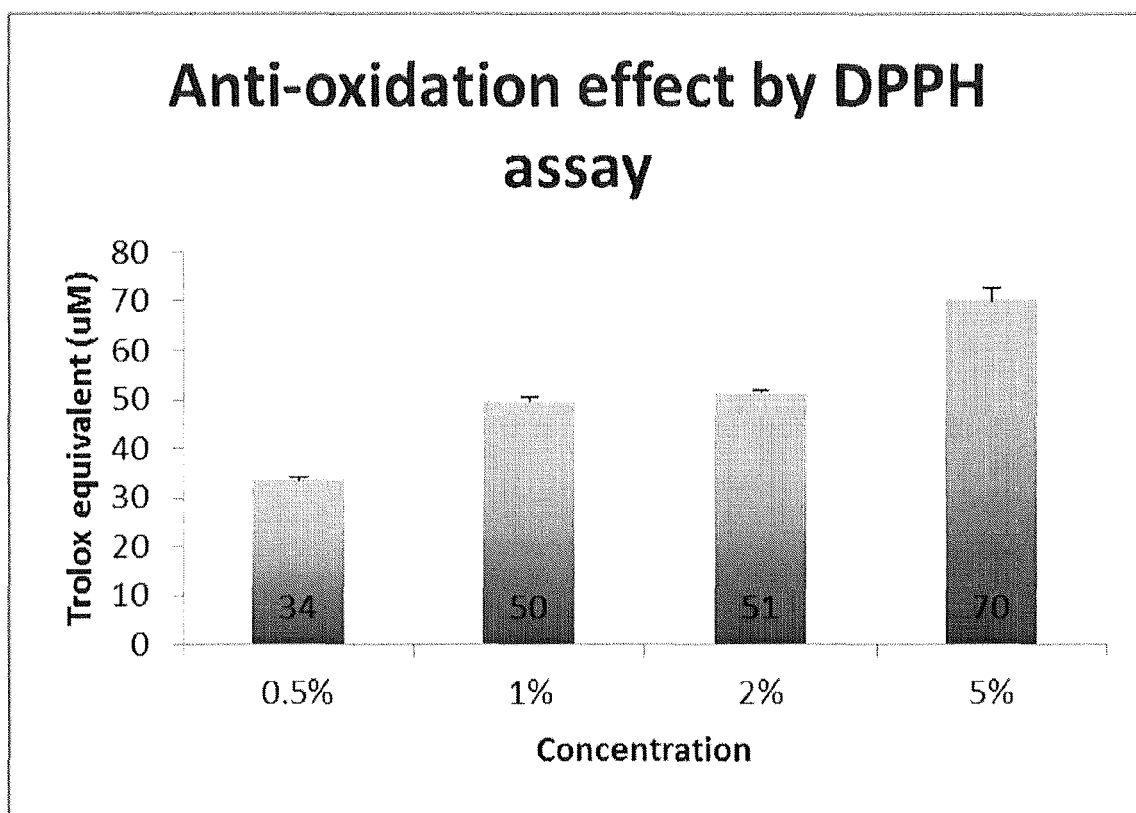

The *Fucus vesiculosus* of the present invention may be naturally occurring (i.e., "wild") or cultivated.

An extract of *Fucus vesiculous*, may be obtained by extraction methods known to those skilled in the art. The extraction may be obtained by aqueous extraction or extraction with an alcohol or a water/alcohol mixture, wherein said alcohol may be isopropanol, ethanol or methanol. Preferably, the extract is from an aqueous extraction.

The *Fucus* extracts of the present invention may be utilized as a cosmetic active ingredient at concentrations between about 0.1% and about 10% by weight of the total composition, preferably between about 0.5% and about 5%, and more preferably between about 0.5% and about 2%. At 1% concentrations, HO-1 expression in keratinocytes is induced by 4 fold (relative to media control) and IL-8 production is inhibited by 60% (relative to control). At 2% concentrations, HO-1 expression in keratinocytes is induced more than 8 fold (relative to media control).

As further shown in the examples and figures, the cosmetic active ingredients of the present invention provide multiple cosmetic benefits when applied to skin under the eyes. More specifically, the present cosmetic active ingredients stimulate HO-1 in the skin cells, and provide very good anti-oxidation efficacy and anti-inflammatory efficacy. The *Fucus* extracts of the present invention have been shown to stimulate collagen to and would have also have a beneficial effect on the appearance of lines and wrinkles. Due to the multiple cosmetic benefits, the extracts of the present invention may be used as the sole cosmetic active ingredient in a cosmetic formulation, but in some embodiments it remains desirable to use such extracts in combination with one or more additional cosmetic active ingredients. Examples of advantageous additional cosmetic active ingredients are skin whitening or skin lightening cosmetic ingredients.

Additional preferred cosmetic compositions may comprise one or more additional marine-derived topical skin care ingredients having additional and/or complementary beneficial skin effects. By way of example, suitable additional marine-derived topical skin care ingredients for use in such topical compositions may include those described in US 2010-0047219 (Ceccoli et al), US 2010-0316720 (Statz et al), US 2009-0142370 (Shih et al), U.S. Pat. No. 7,128,914 (Leclerc et al), U.S. Pat. No. 7,220,517 (Nizard et al), all of which are incorporated herein by reference, and *Chondrus crispus* extract. Many other cosmetically active ingredients are known to a person skilled in the art for improving the health and/or physical appearance of the skin. The skilled person will know how to formulate the cosmetic or dermatological compositions in order to optimize the desired effects.

Cosmetic compositions comprising the extract of the present invention may include cosmetically or dermatologically acceptable ingredients known to those skilled in the art, such as, for example, at least one ingredient selected from the group consisting of preservatives, emollients, emulsifying agents, surfactants, moisturizers, thickening agents, conditioning agents, film-forming agents, stabilizing agents, anti-oxidants, texturizing agents, gloss agents, mattifying agents, solubilizers, pigments, dyes, fragrances and sunscreens. The CTFA Cosmetic Ingredient Handbook, Second Edition (1992) describes various cosmetic and pharmaceutical ingredients which are routinely used in the cosmetics and pharmaceuticals industry which in particular are suitable for topical use and may be used in combination with the active ingredients of the present invention. As used herein, the term "cosmetically or dermatologically acceptable" means suitable for use in contact with skin without undue toxicity, incompatibility, instability, irritation, allergic response, and the like, commensurate with a reasonable benefit to risk ratio.

Advantageously, the compositions cited above are formulated into a form selected from the group consisting of a solution, aqueous or oily, a cream or an aqueous or oily gel, in particular in a pot or a tube, especially a shower gel, a shampoo; a milk; an emulsion, a microemulsion or a nanoemulsion, especially oil-in-water or water-in-oil or multiple or siliconized; a lotion, in particular in a glass or plastic bottle or dispensing bottle or aerosol; an ampoule; a liquid soap; a dermatological cake; a ointment; a foam; an anhydrous product, preferably liquid, paste or solid, for example in the form of a stick; and powders.

In some embodiments, the cosmetic compositions of the present invention are of the type known as anti-wrinkle or anti-aging that are, in particular, intended to be applied on skin terms "aged" (i.e., skin of an individual having a chronological age of 40 or more years). In other embodiments, the cosmetic compositions are products for making up the skin of the face, such as a foundation or concealer or in products for protecting the skin against UV damages, notably a sunscreen or after-sun care product.

A method of cosmetic skin care is also disclosed, comprising the topical application to a the skin of a person in need thereof of a safe and effective amount of a *Fucus vesiculous* extract in order to reduce the appearance of dark circles in skin beneath the eyes. This method is particularly useful for treating aged skin which may have not only dark circles and bags, but also fine lines and wrinkles.

As used herein, the term "safe and effective amount" means an amount of an active ingredient which is high enough to modify the condition to be treated or to deliver the desired skin care beneficial effect, but low enough to avoid serious side effects, at a reasonable benefit to risk ratio within the scope of sound medical judgment. The "safe and effective amount" of an ingredient will vary with the specific ingredient, the ability of the ingredient to penetrate through the skin, the skin condition of the user, and other similar factors known to one skilled in the art.

Although the duration of time necessary to improve the appearance of skin under the eye will vary based on the overall efficacy of the particular cosmetic composition and the amount of *Fucus* extract contained therein, in one preferred embodiment, the method for reducing the appearance of dark circles in skin beneath the eye comprises applying to said skin a safe and effective amount of a cosmetic composition comprising a *Fucus vesiculous* extract at least once a day, wherein the cosmetic composition comprises between about 0.1% and 10% of the *Fucus* extract.

Examples

The present invention is further demonstrated by the way of the following examples, which should not be considered limiting. Unless otherwise stated, the proportions given in any Examples herein are expressed as percentages by weight. The temperature is in degrees Celsius and the pressure is atmospheric pressure.

Extracts

*Fucus vesiculosus* biomass was obtained from commercial suppliers and various extractions of such biomass were made as shown below.

Aqueous Extractions 1.5% coarse ground *Fucus vesiculosus* biomass was added to 95% deionized water and prop mixed overnight at room temperature. The resulting mixture was coarse-filtered through filter socks, then fine-filtered through stacked-disk filters with diatomaceous earth followed by canister filters to final pore size of 0.22 microns.

Polyethylene Glycol (PEG) Extractions

10% coarse ground *Fucus vesiculosus* biomass was added to 90% of a 15% PEG solution and prop mixed overnight at room temperature. The resulting mixture was coarse-filtered through filter socks, then fine-filtered through stacked-disk filters with diatomaceous earth followed by canister filters to final pore size of 0.22 microns.

Evaluation of HO-1 Stimulation, Anti-Oxidavtive Effects and Anti-Inflammatory Effects

*Fucus* extracts were prepared and screened for heme oxygenase 1stimulation, anti-oxidation efficacy, and anti-inflammatory efficacy. Test protocols are described below.

Stimulation of HO-1 Gene Expression by *Fucus* Extract (RT-PCR)

Normal human epidermal keratinocyte and normal human dermal fibroblast cells were treated with aqueous *Fucus* extracts (at 0.5%, 1%, and 2% concentrations) for 24 hours, cells were washed with PBS once, total RNA was extracted from the cells and used as template in RT-PCR reactions using primer sets specific for the heme oxygenase 1 gene. Results were normalized by a house keeping gene and presented as log with a base 2 compared to untreated control. A graph of the results is shown in FIG. 1-A. The same assay was conducted for *Fucus* PEG extracts (at 0.1%, 0.3%, and 1% concentractions. A graph of the results is shown in FIG. 1-B.

Stimulation of HO-1 Protein Expression by *Fucus* Extract in Keratinocytes and Fibroblasts (Western Blot)

Normal Human Epidermal Keratinocytes (NHEK) and normal human fibroblast were treated with aqeous *Fucus* extract (at 1% and 2% concentrations), respectively for 3 days. Cells were then processed for western blot by lysis in RIPA buffer containing a cocktail of protease inhibitors. The lysate was sonicated for 15 seconds, centrifuged 10 minutes at 12000 g, and the supernatants quantified for protein content by BCA assay. Heme oxygenase 1 protein levels were then analyzed by electrophoresing in an 4-20% acrylamide gradient gel, transferring to a nitrocellulose membrane and blotting 90 minutes with mouse anti-human heme oxygenase 1 antibodies and mouse anti-beta actin antibodies (to normalize protein loading). After washing, the membrane was blotted with HRP-linked anti-mouse antibodies for 60 minutes. Heme oxygeanse 1 and beta-actin bands were resolved and quantified by chemiluminescence on a Kodak Image Station 4000R. Results are shown in FIG. 2-A (for keratinocytes) and FIG. 2-B (for fibroblasts) as the normalized intensity of heme oxygenase 1 band.

Anti-Oxidation Assay (DPPH Assay)

The assay was done with the DPPH method. 100 uL of sample or standard (Trolox-Vitamin E) was mixed with 100 ul of 100 uM DPPH solution in a 96 well plate, mix for 20 min at room temperature and absobance was read at 510 nm. Results were presented as trolox equivalent. A graph of the efficacies of aqueous *Fucus* extract at 0.5%, 1%, 2%, and 5% concentrations is shown in FIG. 3.

Anti-Inflammation Assay (IL-8 Assay)

Figure 4:
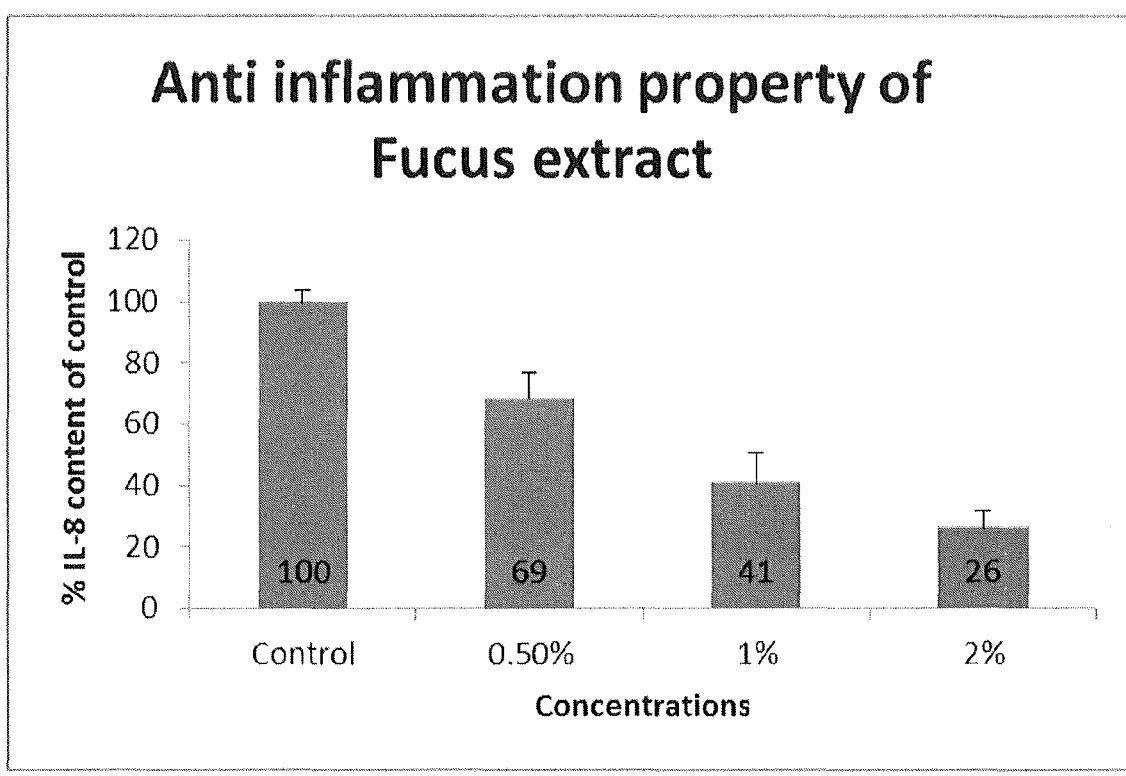
FIG. 4 is a graph showing the anti-inflammatory efficacy of *Fucus vesciculosis* extract.

Normal human epidermal keratinocyte was treated with *Fucus* extract and at the same time stimulated by IL-1b overnight. The IL-8 level in the supernatant was measured by an ELISA kit (R&D system, Minneapolis, Minn. 55413, USA). Results are presented as the percentage of untreated control (no *Fucus* but with IL-1b). A graph of the efficacies of aqueous *Fucus* extract at 0.5%, 1% and 2% concentrations is shown in FIG. 4.

Collagen Stimulation

Figure 5:
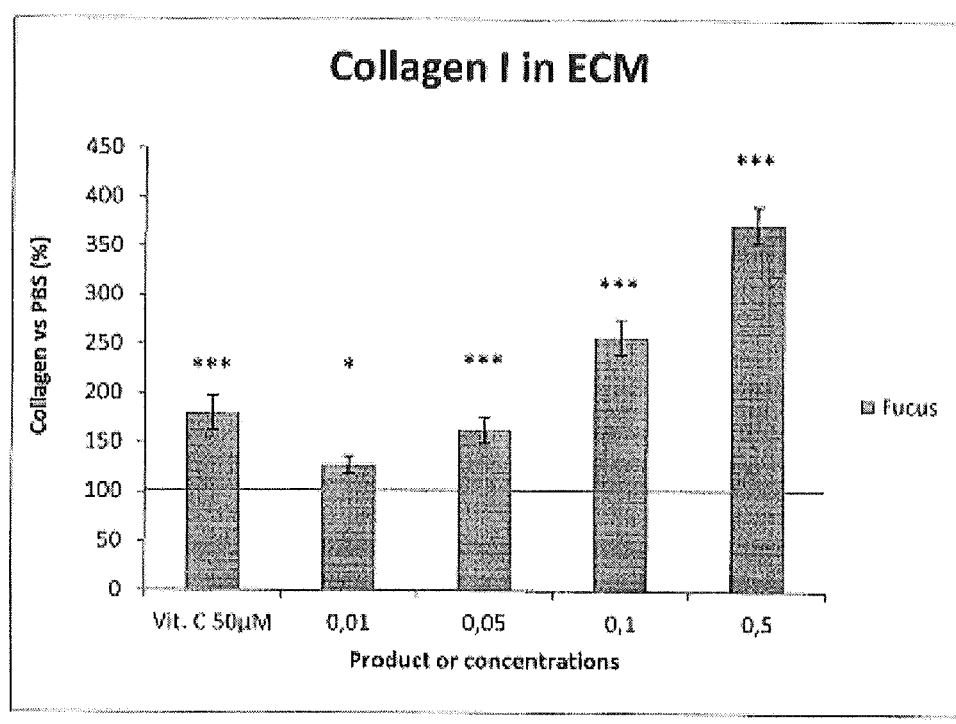
FIG. 5 is a graph showing the collagen stimulation efficacy of *Fucus vesciculosis* extract.

Collagen I was assayed using the method set forth in U.S. patent application Ser. No. 13/528,087, filed Jun. 20, 2012, entitled "Immunoassay method for in vitro measurements", incorporated herein by reference. After treatment with aqueous *Fucus* extract of the present invention, cells were disrupted with dedicated lysis solution and the deposited collagen I was detected by primary antibody human anti-collagen I (Interchim, Montlucon, France) and with the secondary antibody anti-IgG coupled to a DELFIA Europium (Perkin Elmer, Courtaboeuf, France) probe. Europium-related fluorescence, proportional to the quantity of deposited collagen was measured. Results were presented as collagen percentage of PBS control. Results are shown in FIG. 5.

Cosmetic Compositions

An exemplary cream cosmetic product comprising a cosmetic active component of the present invention is as follows:

Liquid Crystal Cream:

Combine phase A, shown in Table 1 below, in larger beaker with prop mixer. Mix until gum is swelled. Heat to 75° C. Combine phase B, shown in Table 1 below, in side beaker, under prop mixer. Heat in water bath to 80° C. until uniform. Add phase B to phase A, mix using Silverson homogenizer (2000-4000 rpm) until uniform. Move to sweep mix (50 rpm) and begin cooling. Below 40° C., add phase C to AB under homogenizer (3000-5000 rpm) until uniform. Move back to sweep and drop at 30° C.

TABLE 1

| PHASE | RAW MATERIAL | LOT# | INCI MOMENCLATURE | % W/W |
|---|---|---|---|---|
| A | 010 Deionized Water | | Water | 67.700 |
| A | 020 Disodium EDTA | | Disodium EDTA | 0.050 |
| A | 030 Butylene Glycol | | Butylene Glycol | 3.000 |
| A | 040 Keltrol CGRD | | Xanthan Gum | 1.000 |
| B | 050 Emulgade PL 68 50 | | Cetearyl Glucoside (and) Cetearyl Alcohol | 5.000 |
| B | 060 Lanette 16 | | Cetyl Alcohol | 4.000 |
| B | 070 Coconut Oil | | Coconut oil | 6.000 |
| B | 080 Luvitol Lite | | Hydrogenated Polyisobutene | 5.000 |
| C | 090 Vitamin E Acetate | | Tocopheryl Acetate | 5.000 |
| C | 100 Symdiol 68T | | Preservative | 1.250 |
| C | 110 Fucus Extract | | | 2.000 |
| | | | | 100.000 |

What is claimed is:

1. A method of increasing heme oxygenase type 1 activity so as to reduce the appearance of dark circles in skin beneath the eye(s) of a subject in need thereof, the method comprising applying to the skin of said subject a safe and effective amount of a topical composition comprising an extract of *Fucus vesiculosus*, wherein the extract is present in an amount from about 0.1 percent to about 10 percent by weight based on total weight of the composition, and wherein the extract is formed by adding a coarse ground biomass of *Fucus vesiculosus* to at least one of deionized water or a polyethylene glycol (PEG) solution for a suitable period of time.

2. A method for catalyzing degradation of heme so as to reduce the appearance of dark circles in skin beneath the eye(s) of a subject in need thereof, the method comprising applying to the skin of said subject a safe and effective amount of a topical composition comprising an extract of *Fucus vesiculosus*, wherein the extract is present in an amount from about 0.1 percent to about 10 percent by weight based on total weight of the topical composition, and wherein the extract is formed by adding a coarse ground biomass of *Fucus vesiculosus* to water and/or polyethylene glycol (PEG) for a suitable period of time.

3. The method of claim 1, wherein the extract is an aqueous extract.

4. The method of claim 2, wherein the extract is present in an amount of about 0.5 percent to about 5 percent by weight, based on the total weight of the topical composition.

5. The method of claim 4, wherein the topical composition is a cream, gel, or lotion product.

6. The method of claim 2, wherein the extract is present in an amount of about 2 percent by weight, based on the total weight of the topical composition.

7. The method of claim 1, wherein the extract of *Fucus vesiculosus* is formed by adding the coarse ground biomass of *Fucus vesiculosus* to the deionized water.

8. The method of claim 1, wherein the extract of *Fucus vesiculosus* is formed by adding the coarse ground biomass of *Fucus vesiculosus* to the PEG solution.

9. The method of claim 2, wherein the extract of *Fucus vesiculosus* is formed by adding the coarse ground biomass of *Fucus vesiculosus* to the water.

10. The method of claim 2, wherein the extract of *Fucus vesiculosus* is formed by adding the coarse ground biomass of *Fucus vesiculosus* to the PEG solution.

* * * * *